United States Patent
Kalchauer et al.

(10) Patent No.: US 7,153,992 B2
(45) Date of Patent: Dec. 26, 2006

(54) PROCESS FOR PREPARING METHYLCHLOROSILANES

(75) Inventors: Wilfried Kalchauer, Burghausen (DE); Jochen Gross, Tuessling (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/341,094

(22) Filed: Jan. 27, 2006

(65) Prior Publication Data

US 2006/0173203 A1    Aug. 3, 2006

(30) Foreign Application Priority Data

Feb. 3, 2005    (DE) ...................... 10 2005 005 052

(51) Int. Cl.
*C07F 7/04*    (2006.01)

(52) U.S. Cl. .................................... 556/473

(58) Field of Classification Search ................. 556/473
See application file for complete search history.

(56) References Cited

U.S. PATENT DOCUMENTS

| | | |
|---|---|---|
| 4,661,613 A | 4/1987 | Prud'Homme et al. |
| 5,306,328 A | 4/1994 | Streckel et al. |

FOREIGN PATENT DOCUMENTS

| | | |
|---|---|---|
| DE | 38 41 417 A1 | 6/1990 |
| DE | 43 42 910 A1 | 9/1994 |
| EP | 0 470 020 | 2/1992 |
| WO | WO 2004/063206 A1 | 7/2004 |

OTHER PUBLICATIONS

Derwent Abstract Corresponding to DE 42 42 910 A1 [AN 1994-295714].
Derwent Abstract corresponding to EP 0 470 020 [AN 1992-043362].
Derwent Abstract corresponding to DE 38 41 417 [AN 1990-180207].
Derwent Abstract corresponding to WO 2004/063206 [AN 2004-462269].
Lewis, K.M. et al., "Catalyzed Direct Reactions of Silicon," Elsevier, Studies in Organic Chemistry 49, 1993, pp. 1-22.
Øye, H.A. et al., "Silicon for Chemical Industry—Geiranger—Norway," Institute of Inorganic Chemistry, The Norwegian Institute of Technology, Jun. 16-18, 1992; pp. 11-23.
Rong, H.M. Dr.—Thesis, "Silicon for the Direct Process to Methylchlorosilanes," Institutt for Uorganisk Kjemi, 1992, Norway.

*Primary Examiner*—Samuel Barts
(74) *Attorney, Agent, or Firm*—Brooks Kushman P.C.

(57) ABSTRACT

The invention relates to a process for the direct synthesis of methylchlorosilanes by reaction of chloromethane with a contact composition comprising silicon, copper catalyst and a total proportion of sodium and potassium of from 10 to 400 ppm.

18 Claims, No Drawings

PROCESS FOR PREPARING METHYLCHLOROSILANES

BACKGROUND OF THE INVENTION

1. Field of the Invention

The invention relates to a process for the direct synthesis of methylchlorosilanes using a contact composition comprising sodium and/or potassium.

2. Background Art

Processes for preparing methylchlorosilanes by reaction of silicon with chloromethane in the Müller-Rochow direct synthesis in the presence of suitable catalysts and catalyst combinations are already known. For example, this is described in CATALYZED DIRECT REACTIONS OF SILICON, K. M. Lewis, D. G. Rethwisch; Elsevier 1993.

In the direct synthesis of methylchlorosilanes, metallic silicon is reacted with chloromethane in the presence of various catalysts, and optionally promoters, with the target product being dimethyldichlorosilane. The mixture of silicon, catalysts and promoters is referred to as the "contact composition". As a worldwide total of over 1,500,000 metric tons of dimethyldichlorosilane is produced annually, very small improvements in the production process, for example an increase in the dimethyldichlorosilane selectivity, an increase in the dimethyldichlorosilane-specific space-time yield, or an increase in the specific raw materials yield, therefore have a large economic effect.

DE 3841417 A1 describes a "silicon atomized by means of inert gas" having an Na content of 0–0.5% and a K content of 0–0.5%. These figures are very imprecise, especially in the light of SILICON FOR THE CHEMICAL INDUSTRY, Geiranger, Norway; Jun. 16–18, 1992; pages 11–23; "Impurity Distribution in Silicon", A. Schei, H. Rong, A. G. Forwald, it is clearly shown in Table 1 and FIG. 1 that in the production of refined, metallurgical silicon, as is used in the direct synthesis, Na and K impurities mainly leave the process via the offgases/dust and are only found to a very small extent in the silicon. A value of <5 ppm is explicitly indicated for Na in silicon. In Harry Morten Rong; SILICON FOR THE DIRECT PROCESS TO METHYLCHLOROSILANES; Doctorate Thesis, 1992, Norway, it is furthermore stated on pages 55–56 that the alkali metals are normally taken off with the offgas in the production of silicon.

European published application EP 470020 A1 states that 0.05–2% by weight of Li, Na, K, Rb or Cs is present in contact compositions, while U.S. Pat. No. 4,661,613 A describes the use of 0.05–4% by weight of Cs in the direct synthesis, with up to 90% by weight of the claimed amount of Cs being able to be replaced by Li, Na, K, Rb. The theoretical Na, K content is thus in the range from 0 to 3.6%. In the concrete examples, cesium is used. WO 2004/063206 describes a contact composition to which from 0.01 to 2% by weight of cesium, potassium or rubidium is added and which forms little carbon. In the actual examples, cesium was added.

SUMMARY OF THE INVENTION

It is an object of the present invention to provide a process for the direct synthesis of methylchlorosilanes by the Müller-Rochow method, which is improved with respect to the preparation of dimethyldichlorosilane. The invention provides a process for the direct synthesis of methylchlorosilanes by reaction of chloromethane with a contact composition comprising silicon, copper catalyst and a total proportion of sodium and potassium of from 10 to 400 ppm.

DETAILED DESCRIPTION OF THE PREFERRED EMBODIMENTS

It has been found that a total content of sodium and potassium of from 10 to 400 ppm in the contact composition has a positive effect on the specific dimethyldichlorosilane formation, especially the amount of $Me_2SiCl_2$ formed per unit mass of silicon used and unit time.

The total content of sodium and potassium in the contact composition is preferably at least 20 ppm. The total content of sodium and potassium in the contact composition is preferably not more than 250 ppm, in particular not more than 100 ppm. The content of sodium or potassium in the contact composition is preferably at least 10 ppm and not more than 300 ppm, preferably not more than 100 ppm, in particular not more than 50 ppm. In particular, the content of potassium is higher than that of sodium, with the sodium content preferably being at least 10 ppm when sodium and potassium are both present.

The content of sodium and potassium in the contact composition is preferably set in a targeted manner by means of suitable measures. Sodium and potassium can be added to the contact composition as the metals, as alloys or as metal compounds, or are preferably introduced together with the raw materials such as silicon and catalysts into the contact composition. In the latter case, the concentrations of sodium and potassium in the contact composition are controlled independently of the content of sodium and potassium in the raw materials via the operating parameters of the methylchlorosilane synthesis. Operating parameters are in this case, for example, the ratio of fresh raw materials fed to silicon-containing solids discharged from the system, for example cyclone dust or filter dust, as described in CATALYZED DIRECT REACTIONS OF SILICON; K. M. Lewis, D. G. Rethwisch; Elsevier 1993, page 18, FIG. 3.

The process can be carried out batchwise or continuously. In industrial production, only the continuous embodiment is employed. Continuous means that the amounts of silicon reacted and any catalysts and promoters carried out with the reaction dust are continually replaced, preferably as pre-mixed contact composition. The continuous direct synthesis is preferably carried out in fluidized-bed reactors in which chloromethane is simultaneously used as a fluidization medium and as a reactant.

The silicon required is milled to a powder beforehand and mixed with copper catalyst and promoters to produce the contact composition. Preference is given to using silicon having a particle size of not more than 700 µm, more preferably a particle size of not more than 500 µm. The silicon used usually has a purity of >98%.

A production campaign for the continuous direct synthesis is started with the induction phase. At the beginning of the induction phase, methyl chloride is passed into the heated contact composition. This is followed by the start-up phase in which crude silane formation commences. The reaction initially proceeds with low selectivity and reactivity. The stable production phase is reached subsequently. Further amounts of silicon and, if appropriate, catalysts and promoters/cocatalysts are continually metered in. The production campaign ends when no more chloromethane is introduced into the contact composition.

During continuous operation of a reactor, the productivity based on the target product dimethyldichlorosilane decreases after a largely stable production phase in a production campaign. For this reason, the production campaign has to be stopped after some time. A production campaign usually lasts for from only a few days to a number of weeks.

After the end of a production campaign, the reactor is emptied, charged again with silicon, copper catalyst and promoters/cocatalysts and brought back to reaction conditions.

In the direct synthesis, unreacted chloromethane, the gaseous methylchlorosilanes and possibly entrained particles leave the reactor. The entrained particles comprise reacted silicon particles, fine silicon particles, catalysts and promoters/cocatalysts. The entrained particles can, if desired, be separated off from the gas stream by means of one or more cyclones, with large entrained particles of contact composition being able to be recirculated to the reactor. The silane is subsequently separated off from residual amounts of dust and unreacted chloromethane and passed to a distillation. Purified, unreacted chloromethane can be fed back into the reactor.

The process is preferably carried out in a fluidized-bed reactor, preferably in the temperature range from 250 to 360° C., in particular from 280 to 330° C. Due to the fact that this is the least complicated, the process is usually carried out at the pressure of the surrounding atmosphere, i.e. at from about 0.1 MPa to 0.5 MPa, but higher pressures can also be employed. It is also possible to use inert gases such as nitrogen or argon in the process. Preference is given to using no inert gas.

The flow rate of the gas stream is, in a preferred embodiment, selected so that a fluidized bed comprising contact composition and gas is formed in the reactor. Unreacted chloromethane and any inert gas and the gaseous methylchlorosilanes leave the reactor. The contact composition is prepared by simple mixing of the individual components at room temperature. A treatment of the contact composition before it is introduced into the reactor is possible but is not carried out in the preferred embodiment.

In the process of the invention, the form of the copper is preferably selected from among metallic copper, copper alloys, copper oxide and copper chloride. Copper oxide can, for example, be copper in the form of copper oxide mixtures and in the form of copper(II) oxide. Copper chloride can be used in the form of CuCl or in the form of $CuCl_2$ with corresponding mixtures also being possible. In a preferred embodiment, the copper is used as copper oxide and/or CuCl. Preference is given to using from 0.3 to 10% by weight, in particular from 0.5 to 7% by weight, of copper catalyst, based on metallic copper and silicon. Particular preference is given to from 0.8 to 5% by weight.

The process of the invention can be carried out using promoters which are preferably selected from among phosphorus, cesium, barium, tin and antimony. The amount of promoters in the contact composition is preferably from 5 to 100 ppm, in particular from 10 to 80 ppm, most preferably from 15 to 620 0 ppm.

In a preferred embodiment of the process of the invention, zinc is used as cocatalyst. Zinc is preferably used in the form of metallic zinc, including zinc alloys, in particular an alloy with copper and optionally, further promoters, zinc oxide or $ZnCl_2$. The amount of zinc in the contact composition is, based on the element, preferably from 0.005 to 1.0% by weight, more preferably from 0.01 to 0.5% by weight, in particular from 0.05 to 0.2% by weight.

Furthermore, it has been found that hydrocarbon formation, in particular isobutane formation, can additionally be reduced at a total content of sodium and potassium of from 10 to 400 ppm in the contact composition in combination with $ZnCl_2$ in the contact composition. The reduced hydrocarbon formation results in a higher raw material yield and reduced consumption of the circulating MeCl gas in MeCl/hydrocarbon formation or a higher reactivity at an unchanged MeCl/hydrocarbon formation. In addition, the proportion of undesirable, unusable high boilers is reduced by means of this combination. This leads to a further increase in the raw material yield and a reduction in disposable costs. Hydrocarbon formation is particularly low when tin is additionally used as promoter.

In the following examples, unless indicated otherwise, all amounts are by mass; all pressures are 0.10 MPa (abs.); and all temperatures are 20° C.

EXAMPLES

The results in the reaction of silicon with chloromethane in the presence of suitable catalysts depend not only on the make-up of the contact composition but also on the construction of the experimental plant and the way in which the experiment is carried out. To eliminate the latter two parameters and to be able to demonstrate the advantages of the invention unambiguously, the experiments described in the following examples were carried out according to the following standardized procedure.

The silicon powder used is commercially available silicon metal, milled and sieved to a particle size in the range from 70 to 240 μm; and the copper oxide is produced as described in U.S. Pat. No. 5,306,328, Example 5. All other chemicals are commercially available in the chemicals trade, e.g. from Fluka Chemie GmbH, Germany. The experimental plant consists of a laboratory fluidized-bed reactor vertical glass tube having an internal diameter of 25 mm and a height of 50 mm provided with heating tape, a gas distributor frit, a distillation head with brine cooling, and a receiver flask.

Standardized Procedure:

Copper catalyst, 0.8 g of metallic zinc as cocatalyst, 8 mg of tin powder and, if appropriate, NaCl and KCl are intimately mixed, mixed with 120 g of silicon, introduced into the reactor and heated to 340° C. under a nitrogen stream of 40 l/h. 40 l/h of chloromethane are subsequently passed through the reactor and the contact composition is heated to 395° C. After an induction time in the range from 2 to 30 minutes, silane formation commences, the reaction temperature is reduced to 360° C., and 50 ml of methylchlorosilanes are collected (start-up phase). A further 30 ml of methylchlorosilanes are subsequently collected. The time taken for these 30 ml of silanes to be formed is designated as the production phase; the productivity (PR2) is calculated according to the formula $$PR2 = \frac{\text{g of methylchlorosilanes in the production phase}}{\text{kg of Si used} \times \text{hours for the production phase}}$$

The specific dimethyldichlorosilane formation (BRM2-spec.) =

$$\frac{PR2 \times \text{concentration of dimethyldichlorosilane in the crude silane}}{100}$$

The silane composition of the 30 ml of methylchlorosilanes was determined in % by weight by GC analysis.

Examples 1 to 9 (Examples 1, 4, 5, 9 are not According to the Invention

It is found that, when comparable Cu catalysts are used, amounts of Na in the contact composition which are too low and too high have adverse effects on the specific dimethyldichlorosilane formation. The silicon used had the following composition: 0.24% of Al; 0.039% of Ca; 0.44% of Fe; 0.046% of Ti; <10 ppm of each of the individual elements Na, K, Cs, Sr, Ba.

TABLE 1

| Ex. | g [Cu] | ppm [Na] | ppm [K] | PR2 | % silane M2 | M2-spec. |
|---|---|---|---|---|---|---|
| 1(C) | 6 g CuO | <10 | <10 | 307 | 84.2 | 258 |
| 2 | 6 g CuO | 25 | <10 | 366 | 83.7 | 306 |
| 3 | 6 g CuO | 50 | <10 | 338 | 82.5 | 279 |
| 4(C) | 6 g CuO | 500 | <10 | 239 | 77.2 | 185 |
| 5(C) | 7.6 g CuCl | <10 | <10 | 336 | 82.2 | 276 |
| 6 | 7.6 g CuCl | 25 | <10 | 351 | 82.2 | 289 |
| 7 | 7.6 g CuCl | 50 | <10 | 408 | 84.8 | 346 |
| 8 | 7.6 g CuCl | 100 | <10 | 371 | 85.6 | 318 |
| 9(C) | 7.6 g CuCl | 500 | <10 | 290 | 80.4 | 233 |

Examples 19 to 28 (Examples 19, 24, 25, 28 are not According to the Invention)

It is found that, when comparable Cu catalysts are used, amounts of Na and K in the contact composition which are too low and too high have adverse effects on the specific dimethyldichlorosilane formation.

The silicon used had the following composition: 0.21% of Al; 0.039% of Ca; 0.32% of Fe; 0.032% of Ti; <10 ppm of each of the individual elements Na, K, Cs, Sr, Ba.

TABLE 2

| Ex. | g [Cu] | ppm [Na] | ppm [K] | PR2 | % of silane M2 | M2-spec. |
|---|---|---|---|---|---|---|
| 19(C) | 6 g CuO | <10 | <10 | 248 | 85.3 | 212 |
| 20 | 6 g CuO | 10 | 15 | 307 | 86.2 | 265 |
| 21 | 6 g CuO | 20 | 30 | 389 | 85.8 | 334 |
| 22 | 6 g CuO | 40 | 60 | 373 | 83.9 | 313 |
| 23 | 6 g CuCl | 100 | 150 | 299 | 82.9 | 248 |
| 24(C) | 6 g CuCl | 200 | 300 | 121 | 83.6 | 101 |
| 25(C) | 7.6 g CuCl | <10 | <10 | 333 | 86.2 | 287 |
| 26 | 7.6 g CuCl | 10 | 15 | 389 | 85.7 | 333 |
| 27 | 7.6 g CuCl | 40 | 60 | 363 | 84.4 | 306 |
| 28(C) | 7.6 g CuCl | 500 | 500 | 144 | 72.1 | 104 |

Examples 30 and 31

In an industrial plant for preparing methylchlorosilanes by the Müller-Rochow method, comprising a fluidized-bed reactor with continuous introduction of contact composition, contact composition recirculation via a cyclone system, dust removal system and gas recirculation, as described, for example, in CATALYZED DIRECT REACTIONS OF SILICON; K. M. Lewis, D. G. Rethwisch; Elsevier 1993, pages 8 to 21, a CuCl/CuO mixture was used as catalyst system under comparable conditions at an Na concentration of 26 ppm and a K concentration of 40 ppm in the contact composition. Sn was used as promoter. The Zn cocatalyst was varied, with the absolute concentration of Zn in the contact composition being kept constant.

Example 30

When metallic Zn was used as cocatalyst, an increase in the hydrocarbon concentration in the recycle gas system in the range from 0.5 to 15% by weight was observed.

Example 31

When $ZnCl_2$ was used as cocatalyst, the increase in hydrocarbon concentration was halved, compared to example 30, to about 0.3–8% by weight, with isobutane representing the main influence. As a result of the increased MeCl partial pressure in the recycle gas, the specific dimethyldichlorosilane space-time yield increased by from 5 to 10% compared to example 30. At the same time, the proportion of undesirable high boilers (boiling point above 71° C.) in the crude silane formed decreased by from 15 to 20% by weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the direct synthesis of methylchlorosilanes, comprising reacting chloromethane with a contact composition comprising silicon, copper catalyst and a total proportion of sodium and potassium of from 10 to 400 ppm based on the total weight of the contact composition.

2. The process of claim 1, wherein the content of potassium is higher than that of sodium.

3. The process of claim 1, wherein copper is present in a form selected from the group consisting of metallic copper, copper alloy, copper oxide, copper chloride, and mixtures thereof.

4. The process of claim 2, wherein copper is present in a form selected from the group consisting of metallic copper, copper alloy, copper oxide, copper chloride, and mixtures thereof.

5. The process of claim 1, wherein at least one promoter selected from the group consisting of phosphorus, cesium, barium, tin and antimony are present.

6. The process of claim 2, wherein at least one promoter selected from the group consisting of phosphorus, cesium, barium, tin and antimony are present.

7. The process of claim 3, wherein at least one promoter selected from the group consisting of phosphorus, cesium, barium, tin and antimony are present.

8. The process of claim 1, wherein zinc is present as a cocatalyst.

9. The process of claim 2, wherein zinc is present as a cocatalyst.

10. The process of claim 3, wherein zinc is present as a cocatalyst.

11. The process of claim 5, wherein zinc is present as a cocatalyst.

12. The process of claim 8, wherein at least some zinc is present in the form of $ZnCl_2$.

13. The process of claim 8, wherein the amount of zinc in the contact composition is, calculated as the metal, from 0.01 to 0.5% by weight.

14. The process of claim 12, wherein the amount of zinc in the contact composition is, calculated as the metal, from 0.01 to 0.5% by weight.

15. The process of claim 5, wherein tin is present as an additional promoter.

16. The process of claim 8, wherein tin is present as an additional promoter.

17. The process of claim 12, wherein tin is present as an additional promoter.

18. The process of claim 13, wherein tin is present as an additional promoter.

* * * * *